United States Patent [19]

Cullinan

[11] Patent Number: 5,043,336

[45] Date of Patent: Aug. 27, 1991

[54] CYCLIC IMIDE DERIVATIVES OF 4-DESACETYL VLB C-3 CARBOXHYDRAZIDE

[75] Inventor: George J. Cullinan, Trafalgar, Ind.

[73] Assignee: Eli Lilly and Company, Indianapolis, Ind.

[21] Appl. No.: 503,638

[22] Filed: Apr. 3, 1990

[51] Int. Cl.$^5$ .................. A61K 31/475; C07D 519/04
[52] U.S. Cl. .................... 514/212; 514/218; 514/283; 540/478
[58] Field of Search ............... 540/478; 514/283, 212, 514/218

[56] References Cited

U.S. PATENT DOCUMENTS

| | | | |
|---|---|---|---|
| 4,166,810 | 9/1979 | Cullinan et al. | 540/478 |
| 4,191,688 | 3/1980 | Conrad et al. | 580/478 |
| 4,203,898 | 5/1980 | Cullinan et al. | 540/478 |
| 4,388,305 | 6/1983 | Trouet et al. | 574/283 |
| 4,596,676 | 6/1986 | Cullinan | 540/478 |
| 4,675,400 | 6/1987 | Cullinan | 540/478 |
| 4,677,030 | 5/1987 | Cullinan | 540/478 |
| 4,801,688 | 1/1989 | Laguzza et al. | 530/391 |

*Primary Examiner*—Diana Rivers
*Attorney, Agent, or Firm*—Joseph A. Jones; Leroy Whitaker

[57] ABSTRACT

Cyclic imide derivatives of 4-desacetyl VLB C-3 carboxydrazide, active anti-tumor agents.

8 Claims, No Drawings

CYCLIC IMIDE DERIVATIVES OF 4-DESACETYL VLB C-3 CARBOXHYDRAZIDE

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leuroformine (Belgian Pat. No. 811,110); leurosidine (vinrosidine) and leurocristine (to be referred to hereafter as vincristine) (both in U.S. Pat. No. 3,205,220); deoxy VLB "A" and "B", Tetrahedron Letters, 783 (1958); 4-desacetoxyvinblastine (U.S. Pat. No. 3,954,773); 4-desacetoxy-3'-hydroxyvinblastine (U.S. Pat. No. 3,944,554); leurocolombine (U.S. Pat. No. 3,890,325) and vincadioline (U.S. Pat. No. 3,887,565). Two of these alkaloids, VLB and vincristine, are now marketed as drugs for the treatment of malignancies, particularly the leukemias and related diseases in humans. The two marketed alkaloids are customarily administered by the i.v. route.

Chemical modification of the Vinca alkaloids has been rather limited. In the first place, the molecular structures involved are extremely complex, and chemical reactions which modify one specific functional group of the molecule without affecting other groups are difficult to develop. Secondly, dimeric alkaloids lacking desirable chemotherapeutic properties have been recovered or produced from *Vinca rosea* fractions or alkaloids, and a determination of their structures has led to the conclusion that these "inactive" compounds are closely related to the active alkaloids, frequently differing only as to stereochemistry at a single carbon. Thus, anti-neoplastic activity seems to be limited to very specific basic structures, and the chances of obtaining more active drugs by modification of these structures would seem to be correspondingly slight. Among the successful modifications of physiologically-active alkaloids has been the preparation of 6,7-dihydro VLB (U.S. Pat. No. 3,352,868) and the replacement of the acetyl group at C-4 (carbon no. 4 of the VLB ring system - see the numbered structure below) with higher alkanoyl group or with unrelated acyl groups. (See U.S. Pat. No. 3,392,173.) Several of these C-4 derivatives are capable of prolonging the life of mice inoculated with P1534 leukemia. One of the C-4 derivatives in which a chloroacetyl group replaces the C-4 acetyl group of VLB is also a useful intermediate for the preparation of structurally modified VLB compounds in which an N,N-dialkylglycyl group replaces the C-4 acetyl group of VLB (See U.S. Pat. No. 3,387,001). C-3 carboxamide and carboxhydrazide derivatives of VLB, vincristine, vincadioline etc. have also been prepared and found to be active anti-tumor agents. (Belgian Pat. No. 813,168.) These compounds are extremely interesting because, for example, the 3-carboxamides of VLB are more active against Ridgeway osteogenic sarcoma and Gardner lymphosarcoma than is VLB itself, the basic alkaloid from which they are derived. Certain of these amide derivatives actually approach the activity of vincristine against the same tumors. One of the amides, 4-desacetyl VLB C-3 carboxamide or vindesine, is currently being marketed for the treatment of malignancies, particularly in leukemias and related diseases. In humans, vindesine appears to have less neurotoxicity than does vincristine and is apparently effective against vincristine-resistant leukemias.

4-Desacetyl VLB C-3 carboxhydrazide is disclosed in Belgian Pat. No. 813,168 as being an active anti-tumor agent against transplanted tumors in mice. It has been shown to be active against Ridgeway osteogenic sarcoma, Gardner lymphosarcoma and P1534(J) leukemia. The search still continues for a more active alkaloid which has less side effects.

SUMMARY OF THE INVENTION

This invention provides compounds of the formula

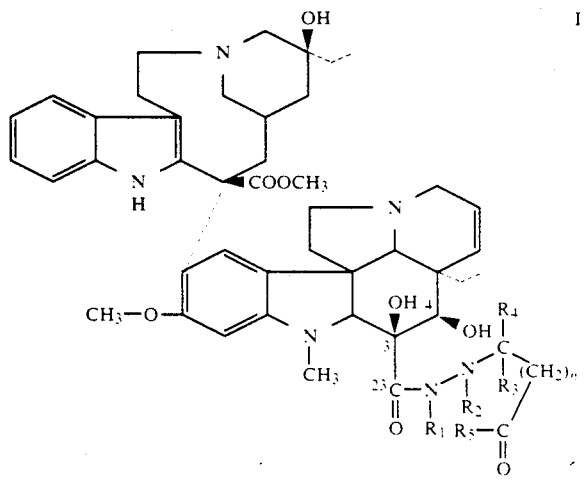

wherein $R_1$ is hydrogen or taken together with $R_5$ to form a direct bond;

$R_2$ is hydrogen, taken together with $R_3$ to form a direct bond or taken together with $R_5$ to form a direct bond ($R_1$ and $R_2$ can not both be taken together with $R_5$ to form a direct bond);

$R_3$ is hydrogen or taken together with $R_2$ to form a direct bond (when $R_2$ and $R_3$ are taken together to form a direct bond, $R_1$ and $R_5$ must be taken together to form a direct bond);

$R_4$ is hydrogen or methyl;

$R_5$ is taken together with $R_1$ to form a direct bond or taken together with $R_2$ to form a direct bond;

n is 2-4;

or an optical isomer of the side chain at the C-3 position;

or a pharmaceutically acceptable salt thereof.

Pharmaceutically acceptable salts of Formula I include salts derived from inorganic acids such as hydrochloric acid, nitric acid, phosphoric acid, sulfuric acid, hydrobromic acid, nitrous acid, phosphorous acid and the like. Such pharmaceutically acceptable salts thus include the sulfate, pyrosulfate, bisulfate, sulfite, bisulfite, nitrate, phosphate, monohydrogenphosphate, dihydrogenphosphate, metaphosphate, pyrophosphate, chloride, bromide, iodide and the like.

DETAILED DESCRIPTION OF THE INVENTION

This invention provides novel 4-desacetyl VLB C-3 carboxhydrazide cyclic imide compounds which are useful as anti-tumor agents.

Examples of the above defined cyclic imide derivatives of 4-desacetyl VLB C-3 carboxhydrazide are described below in Table 1 wherein the terms in the column headings refer to Formula I.

TABLE 1

| $R_1$ | $R_2$ | $R_3$ | $R_4$ | n |
|---|---|---|---|---|
| $R_1$-$R_5$ bond | H | H | H | 2 |
| $R_1$-$R_5$ bond | H | H | $CH_3$ | 2 |
| $R_1$-$R_5$ bond | H | H | H | 3 |
| $R_1$-$R_5$ bond | H | H | $CH_3$ | 3 |
| $R_1$-$R_5$ bond | H | H | H | 4 |
| $R_1$-$R_5$ bond | H | H | $CH_3$ | 4 |
| $R_1$-$R_5$ bond | $R_2$-$R_3$ bond | | H | 2 |
| $R_1$-$R_5$ bond | $R_2$-$R_3$ bond | | $CH_3$ | 2 |
| $R_1$-$R_5$ bond | $R_2$-$R_3$ bond | | H | 3 |
| $R_1$-$R_5$ bond | $R_2$-$R_3$ bond | | $CH_3$ | 3 |
| $R_1$-$R_5$ bond | $R_2$-$R_3$ bond | | H | 4 |
| $R_1$-$R_5$ bond | $R_2$-$R_3$ bond | | $CH_3$ | 4 |
| H | $R_2$-$R_5$ bond | H | H | 2 |
| H | $R_2$-$R_5$ bond | H | $CH_3$ | 2 |
| H | $R_2$-$R_5$ bond | H | H | 3 |
| H | $R_2$-$R_5$ bond | H | $CH_3$ | 3 |
| H | $R_2$-$R_5$ bond | H | H | 4 |
| H | $R_2$-$R_5$ bond | H | $CH_3$ | 4 |

A preferred group of the cyclic imide derivatives of 4-desacetyl VLB C-3 carboxhydrazide is represented by the Formula I wherein $R_1$ and $R_5$ are taken together to form a direct bond.

A further preferred group is represented by the Formula I wherein $R_4$ is methyl.

A particularly preferred group is represented by the Formula I wherein n is 2 or 3.

Preferred compounds represented by Formula I are those which are formed by choosing substituents for $R_1$, $R_5$, $R_4$ and n from the preferred groups represented above.

Another preferred group of the cyclic imide derivatives of 4-desacetyl VLB C-3 carboxhydrazide is represented by the Formula I wherein $R_1$ and $R_3$ are hydrogen and $R_2$ and $R_5$ are taken together to form a direct bond.

A further preferred group is represented by the Formula I wherein $R_4$ is methyl.

Further preferred compounds represented by Formula I are those which are formed by choosing substituents for $R_1$, $R_2$, $R_3$, $R_4$ and $R_5$ from the preferred groups represented above.

The compounds of this invention have been named as derivatives of 4-desacetyl VLB C-3 carboxhydrazide. Systematic naming of these compounds should include a "3-descarbomethoxy" term but this term has been omitted since it is implicit in the name "C-3 carboxhydrazide" in that the C-3 carbomethoxy group of VLB has been replaced. Additionally, an alternative naming system could have been employed; e.g., the compounds may be named as derivatives of 4-desacetyl VLB 23-desmethoxy-23-hydrazide referring to the replacement of the C-23 methoxy by hydrazide. However, this specification names the compounds as C-3 carboxhydrazide derivatives.

Hydrazine contains two nitrogen atoms, which are numbered in a hydrazide as follows

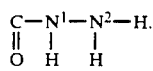

The hydrazide derivatives of this invention are $N^1$ and $N^2$ derivatives.

The compounds of this invention can be prepared by several alternative procedures. The preferred procedure involves the preparation first of 4-desacetyl VLB C-3 carboxhydrazide by the action of anhydrous hydrazine on VLB in a heated reaction vessel employing methanol as a solvent. The reaction of hydrazine with VLB itself serves to hydrolyze the acetoxy group at C-4 and thus the product of the reaction is invariably 4-desacetyl VLB C-3 carboxhydrazide regardless of whether VLB or 4-desacetyl VLB is employed as the starting material. The preparation of compounds of Formula I is carried out with 4-desacetyl VLB C-3 carboxhydrazide, as the starting material.

The compounds of this invention are prepared by reacting 4-desacetyl VLB C-3 carboxhydrazide of Formula II

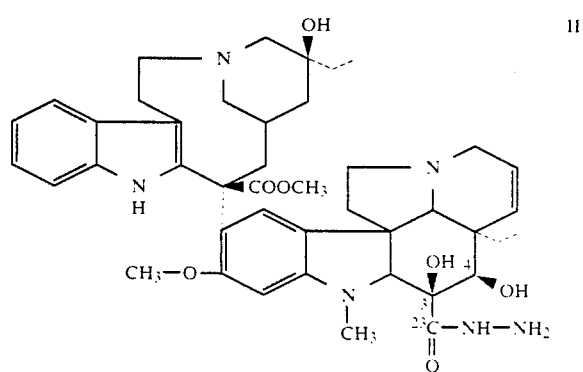

with a keto-acid or an acid-aldehyde of the general structure

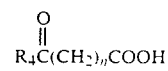

such as succinic semialdehyde, levulinic acid, 4-acetylbutyric acid or 6-ketoheptanoic acid under reflux conditions to form an intermediate of the structure

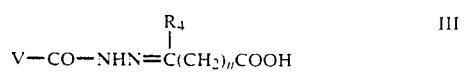

where V represents the vinca alkaloid moiety (all of Formula II except the group attached to C-3), and $R_4$ and n are as defined above. The intermediates of structure III can then be reacted with acetic anhydride or other dehydrating agents to form the compounds of the structure IV

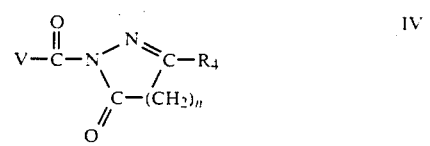

The compounds of structure IV can be reduced with sodium borohydride or other reducing agents to form compounds of the structure V

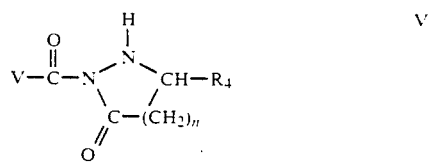

The intermediates of structure III can be reduced with sodium borohydride or other reducing agents to form intermediates of the structure VI

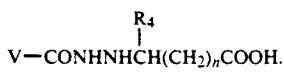

V—CONHNHCH(CH$_2$)$_n$COOH.     VI

The intermediates of structure VI can then be reacted with acetic anhydride or other dehydrating agents to form the compounds of structure VII

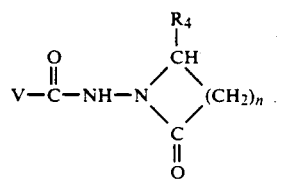

The novel compounds of the invention are useful in the treatment of cancers and as such are preferably prepared for use in formulations suitable for injection. Cancers refer to leukemias, lymphomas, lung adenocarcinoma, testicular carcinoma, breast carcinoma, osteogenic carcinoma, and colorectal carcinoma. Thus the invention could be used in a pharmaceutical formulation, for example an injectable preparation, comprising a compound of the invention together with a pharmaceutically-acceptable carrier or diluent such as are well known in the art. It is preferably in unit dosage form, each dosage containing for example from 1 to 10 mg of the active ingredient.

The novel compounds are effective over a wide dosage range and, for example, for the treatment of adult humans, dosages per week will normally fall within the range of 1 to 10 mg/kg, more usually in the range of from 1 to 5 mg/kg. However it will be understood that the amount of compound actually administered will be determined by a physician in the light of the relevant circumstances, including the condition to be treated and the chosen route of administration.

The invention is illustrated but not limited by the following Examples.

In the following Examples, the terms nuclear magnetic resonance spectra, mass spectra, infra-red spectra, retardation factor, thin layer chromatography, high performance liquid chromatography are abbreviated NMR, MS, IR, R$_F$, tlc and HPLC, respectively.

In addition, the absorption maxima listed for the IR spectra are only those of interest and not all of the maxima observed.

The NMR data for the isomers in Example 1 list only those changes in shift which helped to identify the products as isomers.

The HPLC spectra were obtained by using a Waters Varian Prep 500 with two Pre-Pak 500-Silica columns.

The R$_F$ was obtained by tlc utilizing 5×20 cm, 0.2 mm silica gel plates with fluorescent indicator. All plates were eluted with ethyl acetate:methanol (1:1). The chromatograms were visualized by short wave ultraviolet spectra (UV) and by a spray reagent (H$_3$PO$_4$ Ce(NH$_4$)$_2$(SO$_4$)$_3$). Farnsworth, et al., *Lloydia*, 27(4), 302-314 (1964).

Preparation of Starting Material 4-Desacetyl VLB C-3 carboxhydrazide 65.9 g (0.0725 mole) of vinblastine sulfate was dissolved in 2 L of methanol and 250 g (7.82 mole) of anhydrous hydrazine was added. The reaction mixture was stirred under a nitrogen atmosphere and heated almost to reflux. The reaction was continued for 36 hours and then was allowed to cool. The reaction mixture was filtered and the volatile solvents were removed by evaporation in vacuo, which resulted in a gummy, tan amorphous solid. This product was dissolved in 1 L of methylene chloride and was extracted twice with 500 ml of water. The methylene chloride layer was dried by filtration through anhydrous sodium sulfate and evaporated to dryness in vacuo. This resulted in 49.5 g (0.0648 mole) of crude 4-desacetyl VLB C-3 carboxhydrazide as a tan amorphous powder.

20 g of this crude product was chromatographed (HPLC) on a silica gel column eluted with a linear gradient of 100% ethyl acetate to ethyl acetate:methanol (1:1). The fractions containing the desired product were determined by tlc and combined. The solvents were removed by evaporation in vacuo which yielded 11.68 g (0.0152 mole) of the purified product. This purified product was dissolved in 75 ml of hot methylene chloride and filtered. The product was allowed to crystallize at −20° C. for several hours. The product was filtered and washed with cold methylene chloride and then dried to yield 9.66 g (0.0126 mole) of the desired product as a white crystalline powder.

EXAMPLE 1

4-Desacetyl VLB C-3 N$^2$-(2-methyl-5-oxo-1-pyrrolidinyl)carboxhydrazide

A. 4-Desacetyl VLB C-3 N$^2$-(3-carboxy-1-methylpropylidene)carboxhydrazide 7040 mg (9.15 mmole) of 4-desacetyl VLB C-3 carboxhydrazide was dissolved in 200 ml of toluene and approximately 25 ml of methylene chloride. To this solution was added 1.6 g (13.7 mmole) of levulinic acid and 50 g of anhydrous sodium sulfate. The reaction mixture was heated to reflux and stirred vigorously for a period of four hours. The reaction mixture was allowed to cool and was filtered to remove the sodium sulfate. The resulting solution was evaporated to dryness in vacuo. This yielded a white amorphous powder which was used in further reactions.

R$_F$=0.13

B. 4-Desacetyl VLB C-3 N$^2$-(3-carboxy-1-methylpropyl)carboxhydrazide

The resulting product of Example 1A, 4-desacetyl VLB C-3 N$^2$-(3-carboxy-1-methylpropylidene)carboxhydrazide, was dissolved in 100 ml of absolute ethanol and a small amount of methylene chloride. The reaction solution was cooled to 0° C. in an ice bath. The reaction solution was placed under a nitrogen atmosphere and stirred, while adding 5000 mg (130 mmole) of sodium borohydride. The reaction was allowed to proceed for 20 hours and was evaporated to dryness in vacuo. The reaction mixture was redissolved in 50 ml of 1N hydrochloric acid and made basic with the addition of a saturated solution of sodium bicarbonate. The product was extracted with 50 ml of methylene chloride. The methylene chloride solution was dried by filtration through anhydrous sodium sulfate and was evaporated to dryness in vacuo. The product was further purified by HPLC on a silica gel column eluted with a linear gradient of 100% ethyl acetate to ethyl acetate:methanol (1:1). This yielded 2500 mg of the desired product.

IR: (CHCl$_3$) $\nu$(COO) 1720 and 1740 cm$^{-1}$, (CON) 1660 cm$^{-1}$.

MS: m/e 850 (m - 18, loss of H$_2$O).

pKa: (66% DMF) 5.3, 6.9, and 7.9.

C. 4-Desacetyl VLB C-3 N$^2$-(2-methyl-5-oxo-1-pyrrolidinyl)carboxhydrazide 1200 mg (1.4 mmole) of 4-desacetyl VLB C-3 N$^2$-(3-carboxy-1-methylpropyl)carboxhydrazide was dissolved in 50 ml of pyridine and 410 mg (4.1 mmole) of acetic anhydride was added. The reaction mixture was sealed under nitrogen and allowed to react at room temperature for 20 hours. The progress of the reaction was monitored by tlc, and an additional 100 mg (1.0 mmole) of acetic anhydride was added. After several hours, the reaction mixture was evaporated to dryness in vacuo. The product was further purified by chromatography (HPLC) over a silica gel column eluted with a linear gradient of ethyl acetate (100%) to ethyl acetate:methanol (1:1). The product of this reaction was in fact two compounds, which are isomers at the secondary carbon in the lactam ring. The reaction yielded 370 mg of Isomer I and 240 mg of Isomer 2.

Isomer 1

IR: (CHCl$_3$) $\nu$(CON) 1690 cm$^{-1}$, (COO) 1725 cm$^{-1}$.

MS: m/e 850 (m).

$^1$NMR (300 MHz, CDCl$_3$) $\delta$ 1.20 (doublet, J = 6 Hz).

Isomer 2

IR: (CHCl$_3$) $\nu$(CON) 1690 cm$^{-1}$, (COO) 1725 cm$^{-1}$.

MS: m/e 850(m)

$^1$H NMR (300 MHz, CDCl$_3$) $\delta$ 1.28 (doublet, J = 6 Hz)

EXAMPLE 2

4-Desacetyl VLB C-3 N$^2$-(2-methyl-5-oxo-1-pyrrolidinyl)carboxhydrazide (Isomer 1) sulfate salt 250 mg of Isomer 1 was dissolved in 50 ml of ethanol. The initial pH of 8.5 was adjusted to 4.2 with 2% sulfuric acid in ethanol. The reaction mixture was evaporated to dryness and triturated with ether and then was evaporated to dryness in vacuo.

R$_F$ = 0.63

EXAMPLE 3

4-Desacetyl VLB C-3 N$^2$-(2-methyl-5-oxo-1-pyrrolidinyl)carboxhydrazide (Isomer 2) sulfate salt 180 mg of Isomer 2 was dissolved in 50 ml of ethanol. The initial pH of 8.5 was adjusted to 3.5 with 2% sulfuric acid in ethanol. The reaction mixture was evaporated to dryness and triturated with ether and then was evaporated to dryness in vacuo.

R$_F$ = 0.46

EXAMPLE 4

4-Desacetyl VLB C-3 N$^1$-(4,5,6,7-tetrahydro-3-methyl-7-oxo-1H-1,2-diazepin-1-yl)carboxhydrazide A. 4-Desacetyl VLB C-3 N$^2$-(4-carboxy-1-methylbutylidene)carboxhydrazide 1100 mg (1.43 mmole) of 4-desacetyl VLB C-3 carboxhydrazide was dissolved in 25 ml of methylene chloride and 100 mg (7.7 mmole) of 4-acetylbutyric acid and then 250 mg of anhydrous sodium sulfate was added to the reaction mixture. The reaction mixture was sealed under nitrogen and the reaction was allowed to continue at room temperature for a period of three days. The reaction mixture was filtered and the filtrate was washed with a saturated solution of sodium bicarbonate. The methylene chloride layer was dried by filtration through anhydrous sodium sulfate and the solvate was removed by evaporation in vacuo. The resulting product (930 mg) was an amorphous solid.

IR: (CHCl$_3$) $\nu$(CON) 1685 cm$^{-1}$, (COO) 1720 and 1735 cm$^{-1}$.

pKa: (66% DMF) 5.1, 6.6, and 7.7.

B. 4-Desacetyl VLB C-3 N$^1$-(4,5,6,7-tetrahydro-3-methyl-7-oxo-1H-1,2-diazepin-1-yl)carboxhydrazide 770 mg (0.88 mmole) of 4-desacetyl VLB C-3 N$^2$-(4-carboxy-1-methylbutylidene)carboxhydrazide was dissolved in 50 ml of methylene chloride and 110 mg (1.1 mmole) of acetic anhydride was added. The reaction was allowed to continue for 20 hours, at room temperature and sealed under nitrogen. The reaction solution was washed with 50 ml of water and dried by filtration through anhydrous sodium sulfate. The product was further purified by chromatography (HPLC) over a silica gel column eluted with a linear gradient of ethyl acetate (100%) to ethyl acetate:methanol (2:1). Combination of the desired fractions and evaporation of the solvents in vacuo yielded 300 mg of the desired product.

MS: m/e 862 (m).

R$_F$ = 0.61

EXAMPLE 5

4-Desacetyl VLB C-3 N$^1$-(4,5,6,7-tetrahydro-3-methyl-7-oxo-1H-1,2-diazepin-1-yl)carboxhydrazide sulfate salt 54 mg of 4-desacetyl VLB C-3 N$^1$-(4,5,6,7-tetrahydro-3-methyl-7-oxo-1H-1,2-diazepin-1-yl)-carboxhydrazide was dissolved in ethanol. The initial pH of 7.8 was adjusted to 4.2 with 2% sulfuric acid in ethanol. The solvent was removed by evaporation with a nitrogen stream and further evaporated to dryness in vacuo. This yielded 30 mg of white amorphous powder.

EXAMPLE 6

4-Desacetyl VLB C-3 N$^2$-(hexahydro-2-methyl-7-oxo-1H-azepin-1-yl)carboxhydrazide A. 4-Desacetyl VLB C-3 N$^2$-(5-carboxy-1-methylpentylidene)carboxhydrazide 4000 mg (5.2 mmole) of 4-desacetyl VLB C-3 carboxhydrazide was dissolved in 250 ml of toluene. To this solution was added 2000 mg (14 mmole) of 6-ketoheptanoic acid and 5000 mg of anhydrous sodium sulfate. The reaction mixture was stirred vigorously and heated to reflux. The reaction was kept under a nitrogen atmosphere for about 20 hours. The reaction was allowed to cool and was filtered. The filtrate was evaporated to dryness in vacuo, yielding 4700 mg of amorphous powder. This powder was dissolved in 50 ml of methylene chloride and further purified by chromatography (HPLC) over a silica gel column eluted with a solvent of ethyl acetate:methanol (1:1). The desired fractions were determined by tlc and combined. The combined fractions were evaporated to dryness in vacuo and yielded 3410 mg of desired product.

MS: m/e 895 (m+H).

pKa: (66% DMF) 5.3, 7.0, and 8.1.

B. 4-Desacetyl VLB C-3 $N^2$-(5-carboxy-1-methylpentyl)carboxhydrazide 2000 mg (2.2 mmole) of 4-desacetyl VLB C-3 $N^2$-(5-carboxy-1-methylpentylidene)carboxhydrazide was dissolved in 60 ml of absolute ethanol and 200 mg (5.2 mmole) of sodium borohydride was added. The reaction mixture was placed under a nitrogen atmosphere, stirred and allowed to react for 20 hours at room temperature. The reaction mixture was evaporated to dryness in vacuo and redissolved in 50 ml of 1N hydrochloric acid. This solution was made basic with saturated sodium bicarbonate and extracted with 50 ml of methylene chloride. The methylene chloride extract was dried by filtration through anhydrous sodium sulfate and evaporated to dryness in vacuo, which resulted in 1470 mg of the desired product.

MS: m/e 896 (m).
$R_F$ = 0.22.

C. 4-Desacetyl VLB C-3 $N^2$-(hexahydro-2-methyl-7-oxo-1H-azepin-1-yl)carboxhydrazide 680 mg (0.76 mmole) of 4-desacetyl VLB C-3 $N^2$-(5-carboxy-1-methylpentyl)carboxhydrazide was dissolved in 50 ml of methylene chloride. 300 mg (3.0 mmole) of N-methylmorpholine and 260 mg (1.9 mmole) of isobutyl chloroformate were also added. The reaction was allowed to proceed at room temperature while sealed under nitrogen. After 20 hours the reaction mixture was evaporated to dryness.

IR: (CHCl$_3$) $\nu$(CON) 1680 cm$^{-1}$, (COO) 1732 cm$^{-1}$
MS: m/e 879 (m+1)

EXAMPLE 7

4-Desacetyl VLB C-3 $N^2$-(hexahydro-2-methyl-7-oxo-1H-azepin-1-yl)carboxhydrazide sulfate salt All of the 4-desacetyl VLB C-3 $N^2$-(hexahydro-2-methyl-7-oxo-1H-azepin-1-yl)carboxhydrazide prepared from Example 6 was dissolved in 50 ml of ethanol. The initial pH of 4.9 was adjusted to 3.6 with 2% sulfuric acid in ethanol. An additional 0.5 ml of the 2% sulfuric acid was added, because the trial test of the water solubility of the salt revealed that it was not completely soluble. This material was evaporated to dryness in vacuo, which yielded 750 mg of the title compounds.

$R_F$ = 0.55

The compounds of the present invention inhibit the growth of human leukemic cells (CCRF-CEM cell line). The CEM cells were grown in RPMI 1640 media (MA Bioproducts) at 37° C. in humidified atmospheric conditions of 95% air and 5% carbon dioxide. The cells were grown in static suspension and maintained in log growth phase at a concentration of 3-7×10$^5$ cells/ml. The cells were dispersed in wells at a concentration of 4.8×10$^4$/well. The drug was dissolved in dimethyl sulfoxide or water and was added at different dilutions to the cluster plates (wells). The cluster plates were incubated at 37° C. for 72 hours. After 72 hours the wells were read using a ZBI Coulter particle counter. Table 2 below gives the results of such testing of several compounds represented by Formula I above. In the table, Column 1 gives the name of the compound and Column 2 gives the IC$_{50}$ (concentration giving 50% growth inhibition) in $\mu$g/ml.

TABLE 2

| CCRF - CEM Cytotoxicity Assay | |
|---|---|
| Compound Name | IC$_{50}$ $\mu$g/ml |
| 4-Desacetyl VLB C-3 $N^2$-(2-methyl-5-oxo-1-pyrrolidinyl)carboxhydrazide (Isomer 1) sulfate salt | 0.1 |
| 4-Desacetyl VLB C-3 $N^2$-(2-methyl-5-oxo-1-pyrrolidinyl)carboxyhydrazide (Isomer 2) sulfate salt | 0.09 |
| 4-Desacetyl VLB C-3 $N^1$-(4,5,6,7-tetrahydro-3-methyl-7-oxo-1H-1,2-diazepin-1-yl)carboxhydrazide sulfate salt | 0.019 |
| 4-Desacetyl VLB C-3 $N^2$-(hexahydro-2-methyl-7-oxo-1H-azepin-1-yl)carboxhydrazide sulfate salt | 0.0056 |

I claim:
1. A compound of the formula:

wherein $R_1$ is taken together with $R_5$ to form a direct bond;
$R_2$ is hydrogen or taken together with $R_3$ to form a direct bond;
$R_3$ is hydrogen or taken together with $R_2$ to form a direct bond;
$R_4$ is hydrogen or methyl;
$R_5$ is taken together with $R_1$ to form a direct bond;
n is 2-4;
or an optical isomer of the side chain at the C-3 position;
or a pharmaceutically acceptable salt thereof.

2. A compound of claim 1 wherein $R_2$ and $R_3$ are hydrogen.
3. A compound of claim 2 wherein $R_4$ is methyl.
4. A compound of claim 3 wherein n is 3.
5. A compound of claim 1 wherein $R_2$ is taken together with $R_3$ to form a direct bond.
6. A compound of claim 5 wherein $R_4$ is methyl.
7. A compound of claim 6 wherein n is 3.
8. A pharmaceutical composition comprising an effective amount of a compound of claim 1 and a parenterally-administerable medium.